(12) United States Patent
Walsh et al.

(10) Patent No.: US 9,196,175 B2
(45) Date of Patent: Nov. 24, 2015

(54) ERGONOMIC SENSOR PAD WITH FEEDBACK TO USER AND METHOD OF USE

(76) Inventors: Michael C. Walsh, San Diego, CA (US); Sean Colford, San Diego, CA (US); Ethan Epstein, San Diego, CA (US); Brandon Loye, San Diego, CA (US); Rhonda Epstein, San Diego, CA (US); Matthew Davis, Santa Barbara, CA (US); Wesley Koga, Orange, CA (US); Alexander Saal, Los Angeles, CA (US); Victor Tung, Rowland Heights, CA (US); Frank Winter, San Diego, CA (US)

( * ) Notice: Subject to any disclaimer, the term of this patent is extended or adjusted under 35 U.S.C. 154(b) by 1275 days.

(21) Appl. No.: 13/074,482

(22) Filed: Mar. 29, 2011

(65) Prior Publication Data
US 2011/0275939 A1 Nov. 10, 2011

Related U.S. Application Data

(60) Provisional application No. 61/282,768, filed on Mar. 30, 2010.

(51) Int. Cl.
G09B 19/00 (2006.01)
A61B 5/00 (2006.01)
A47C 31/12 (2006.01)

(52) U.S. Cl.
CPC ............ *G09B 19/003* (2013.01); *A47C 31/126* (2013.01); *A61B 5/4561* (2013.01)

(58) Field of Classification Search
CPC ..................... A61B 5/1116; A61B 2562/0219; A63B 23/0244; A63B 2071/0627; A63B 69/3608
USPC ............................. 340/500, 540, 573.1, 573.7
See application file for complete search history.

(56) References Cited

U.S. PATENT DOCUMENTS

| 4,007,733 A | 2/1977 | Celeste et al. |
| 6,669,286 B2 | 12/2003 | Iusim |

(Continued)

*Primary Examiner* — James Yang
(74) *Attorney, Agent, or Firm* — Lapple Ubell IP Law, LLP; Matthew Lapple (57) ABSTRACT

A portable system is provided for sensing and training a user to maintain correct posture while seated in a chair with a seat portion and a back portion. The system includes a first pad attachable to the seat portion of a chair, said first pad having a front area and a rear area, and a second pad attachable to the back portion of a chair and having a lower area and an upper area. There is a first sensor located in the first pad capable of sensing that a user is seated in the seat portion of the chair, a second sensor located in the first pad capable of sensing whether the lower posterior portion of the user's body is in contact with the rear area of the first pad, a third sensor operably attached to the lower area of the second pad capable of sensing whether the user's lumbar region is in contact with the second pad, a fourth sensor operably attached to the upper area of the second pad capable of sensing the distance between the user's upper back and the upper area of the second pad and a neck-position sensor operably attached to the second pad and capable of sensing the distance between the neck-position sensor and the user's neck. The system also includes a microprocessor operably connected to the first sensor, second sensor, third sensor, fourth sensor and neck-position sensor and capable of collecting data from each of the first sensor, second sensor, third sensor, fourth sensor and neck position sensor. The system also includes software for a personal computer, which configures the personal computer to receive the data from the microprocessor and to display the data received from the microprocessor, so that the user can utilize the ergonomic seat pad to receive feedback regarding his posture and over time, improve his posture.

1 Claim, 9 Drawing Sheets

(56) References Cited

U.S. PATENT DOCUMENTS

| | | | |
|---|---|---|---|
| 6,673,027 B2 | 1/2004 | Fischer | |
| 7,029,031 B2* | 4/2006 | Moisel | G01V 8/20 250/221 |
| 7,161,490 B2* | 1/2007 | Huiban | A47C 9/002 340/10.52 |
| 7,471,290 B2 | 12/2008 | Wang et al. | |
| 2005/0006941 A1* | 1/2005 | Park | B60N 2/4852 297/406 |
| 2005/0067816 A1* | 3/2005 | Buckman | A41D 13/018 280/730.1 |
| 2006/0175888 A1* | 8/2006 | Droche | 297/463.1 |
| 2008/0049020 A1* | 2/2008 | Gusler et al. | 345/427 |
| 2009/0058661 A1* | 3/2009 | Gleckler | A61B 5/103 340/573.7 |
| 2010/0045454 A1* | 2/2010 | Knight et al. | 340/521 |

\* cited by examiner

- Force Sensitive Resistor used to detect when and how much pressure is applied in lumbar region
- Able to detect pressure above. 1kg/cm$^3$ and below 10kg/cm$^3$

ERGONOMIC SENSOR PAD WITH FEEDBACK TO USER AND METHOD OF USE

CROSS-REFERENCE TO RELATED APPLICATIONS

This patent application is related to and claims the benefit of provisional patent application Ser. No. 61/282,768.

FIELD OF THE INVENTION

This invention is generally related to the field of ergonomic devices and methods useful for improving posture. More specifically, this invention is related to apparatus and methods for sensing when a user is seated in a chair at a computer workstation in an ergonomically correct position with proper posture, monitoring the user's posture over time and reporting the results of the monitoring to the user.

BACKGROUND OF THE INVENTION

Each year tens of thousands of people are diagnosed with Repetitive Stress Injuries (RSI). RSI are a group of conditions caused by placing excessive stress or repetitive motion on a joint or a muscle. According to the Occupational Safety and Health Association (OSHA) RSI is leading work related health problem in the United States. RSI are reported to cost the government and businesses billions of dollars each year.

In the 1970's, the average age for someone to develop RSI was in the late 30's-early 40's. Now the average age for developing RSI is in the early-to-mid 20's.

Ergonomic disorders account for most of the RSI in the United States. Incorrect ergonomics and improper posture at computer workstations are contributing to increases in the number of reported health problems and repetitive stress injuries. It has been reported that 67% of adult computer users had experienced neck and upper limb pain in the previous month. Today, this number is greater due to the increase of computer use daily life.

Figure 1:
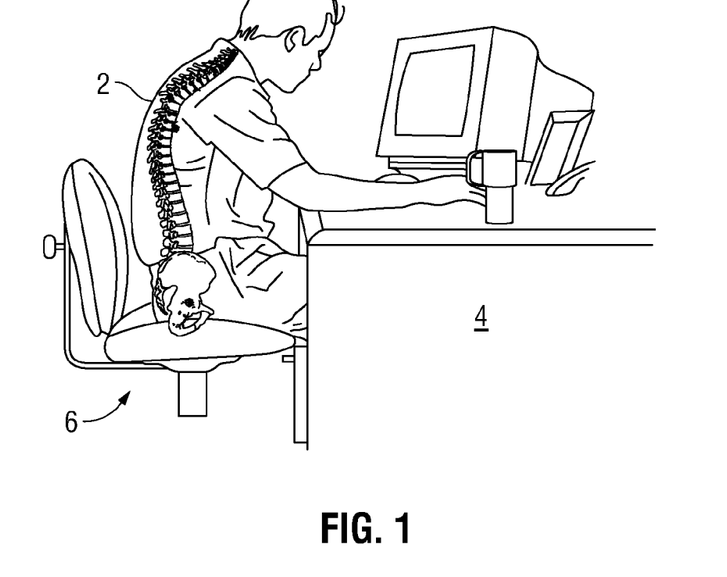
FIG. 1 provides an illustration of a commonly adopted ergonomically incorrect posture, referred to as the "C-Spine" position.
Figure 2:
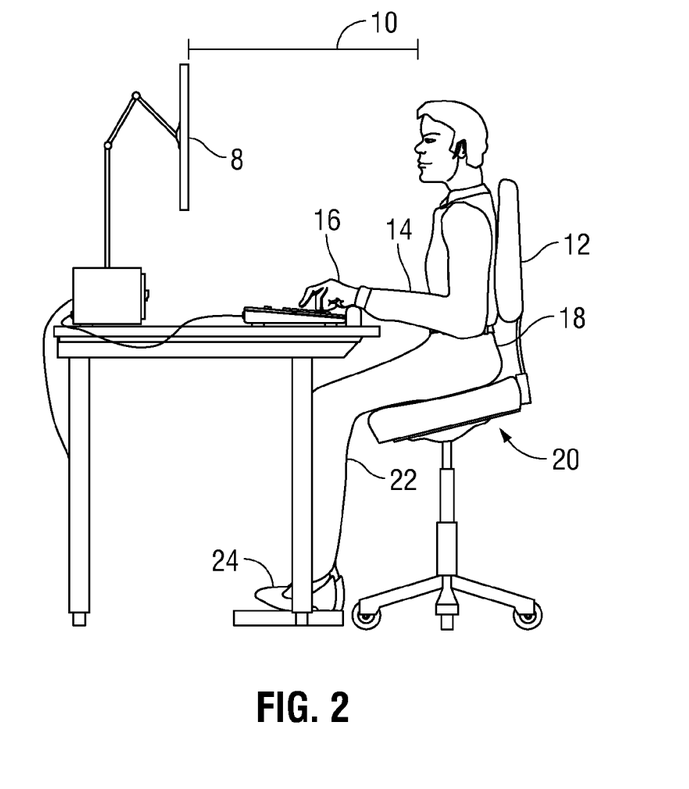
FIG. 2 provides an illustration of ergonomically correct posture for a person seated at a computer work station, referred to as the "S-Spine" position.

The following are risk factors that lead to musculoskeletal pain that lead to computer related injuries (CRI): (a) awkward postures, (b) poorly designed workstations; (c) inadequate seating; (d) poor lighting; and (e) glare. FIG. 1 illustrates a rounded and dysfunctional spinal posture, commonly referred to as a "C-Spine" position 2 which is the partial result of the poorly designed workstation 4 and inadequate seating 6. In contrast, FIG. 2 illustrates an ergonomically correct posture, referred to as a "S-Spine" position. An ergonomically correct posture normally requires and includes (a) proper placement of the buttocks or posterior against the back of the seat pad; (b) a supported lumbar region; (c) sitting erect with the shoulders in line with the pelvis and slightly apart from the seat back; and (d) an erect neck posture, in line with the shoulders and pelvis. In addition, FIG. 2 also illustrates a number of the important adjustments and positioning necessary to achieve this ergonomically correct posture while sitting at a computer workstation. These important adjustments include: (a) having the screen at eye level 8; (b) having the screen at an arm's length distance 10 from the user; (c) a chair with lumbar support 12; (d) arms close to the body and elbows at 90 degrees 14; (e) keeping the wrists straight, with a wrist rest if necessary 16; (f) the buttocks or posterior placed at the back of the chair 18; (g) use of an adjustable chair for correct back support, height and forward pelvic tilt 20; (h) a knee angle greater than 90 degrees 22; and (1) feet flat, with a foot rest if necessary 24.

There is often a ten to fifteen year latency before RSI injuries start to develop. This means that it is important to encourage the development of correct posture habits as early as possible. Childhood back, neck and shoulder pain have been found to be a predictor of adult back, neck and shoulder pain. It is thus important to address the causes of discomfort at a young age in order to prevent musculoskeletal injuries in adulthood. On an increasing basis, children are using computers at younger and younger ages which make them more susceptible to poor posture and RSI when they are older. In 2003, it was found that 91% of children in the U.S. ages 3-18 used computers. Similar statistics are found in Canada, Australia, and other industrial countries. Approximately 80% of children first use a computer in kindergarten, and by the time they reach high school, approximately 97% regularly use computers. University students report that using a computer from young ages causes a habituation and cumulative effect that makes them more likely to have computer related injuries when they are older.

Studies of school age students show that children do experience musculoskeletal discomfort similar to that of adults during computer use and in fact, children are experiencing significant musculoskeletal discomfort associated with computer use.

In studies and surveys done on children, an average of 60% of students reported discomfort associated with computer use. Students are sitting in schools with poorly aligned posture and improper workstation ergonomics. In one study, for example, it was found that no student was found to have acceptable posture. Aside from actual furniture, other issues such as the location of computer screens and documents and the type of keyboards and other input devices that are most appropriate, have seldom been considered.

Ergonomic intervention and education have been shown to reduce discomfort caused by frequent computer use. In one study, when students started to use adjustable tables and chairs, the muscle tension level fell significantly, while the control group showed an increase of head ache, and muscle pain. Another study reported that students that received ergonomic and educational interventions showed a significant decrease in discomfort/pain, with 41% reporting discomfort/pain at the start of the study, down to 18% after year two and 8% after year three.

Accordingly, there is a need for an effective device and method that can be used to train users, including children and young adults, to maintain correct posture while seated at a computer workstation.

BRIEF SUMMARY OF INVENTION

Figure 3A:
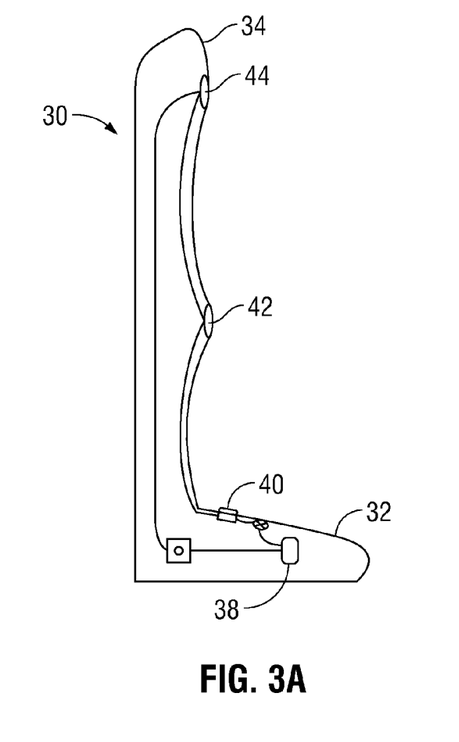
FIG. 3A provides a cross-section of a side view of an embodiment of an ergonomic seat pad of the present invention.
Figure 3B:
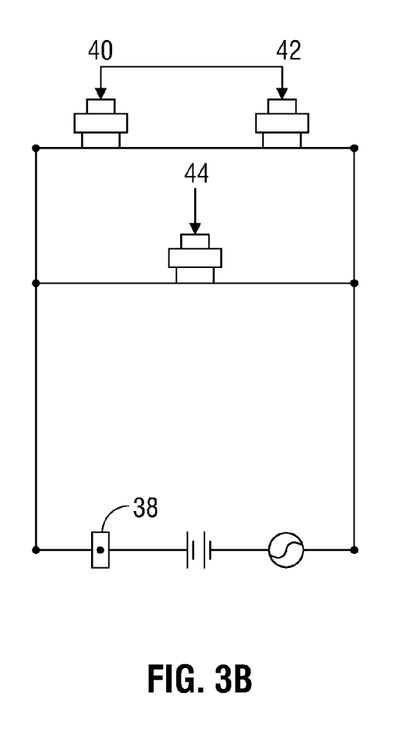
FIG. 3B provides an illustration of a schematic diagram of circuits for sensors of an ergonomic seat pad of the present invention.
Figure 4:
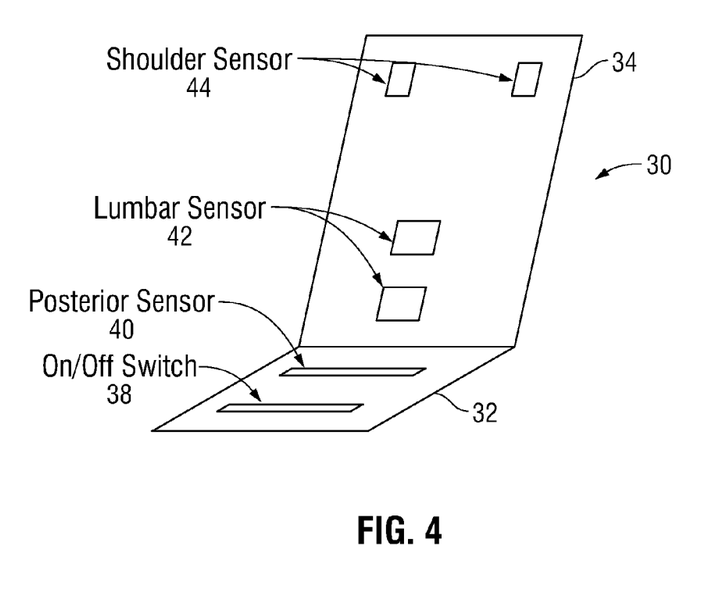
FIG. 4 provides an illustration of a schematic diagram of an embodiment of an ergonomic seat pad of the present invention, showing exemplary positions for the sensors of the ergonomic seat pad.

The ergonomic seat pad of the present invention is a portable ergonomic seat cushion. As illustrated in FIGS. 3A, 4, 6, 11 and 12, it can be designed to fit most chairs and can be adjustable to accommodate people of all sizes. The purpose of the ergonomic seat pad of the present invention is to assist and teach the user to sit at a computer workstation or other location with correctly aligned posture. This helps prevent the development of Repetitive Stress Injuries to the neck, back and extremities. As shown in FIGS. 3A, 3B and 4, the ergonomic seat pad of the present invention includes electrical switches or other sensors embedded into its cushions. These switches or sensors can, for example, cause a vibration or beep to alert the user if s/he moves out of the proper sitting position, thus giving the user continuous feedback about their posture. Preferably, the ergonomic seat pad includes a microprocessor for gathering data from the switches or sensors and for transmitting this data to a personal computer. In turn, preferably, the personal computer is configured to record this data, to display it on a graphical user interface, and to provide both visual and audible feedback to the user so that the user can learn to maintain an ergonomically correct posture when seated.

The ergonomic seat pad of the present invention can assist in creating a clear path to help people learn and maintain healthier sitting habits and, thus, reduce risk of future injury. In businesses environments, this solution can help employees to create better postural habits and to reduce the vast number of RSI. Physical therapists would have a method to help patients with RSI and other ergonomic disorders. The present invention could be used in schools as a means to assist students to create positive posture habits that would benefit them throughout their lives. Affecting students at an early age is paramount to solving the increasing problem of RSIs in our workforce. This in turn would help people live healthier, more enjoyable lives, allow employees to be more productive, and save the government, employers and individuals millions of dollars each year.

BRIEF DESCRIPTION OF THE DRAWINGS

The attached figures and drawings show, as illustrative examples, embodiments of the present invention.

DESCRIPTION OF EMBODIMENTS

Figure 6:
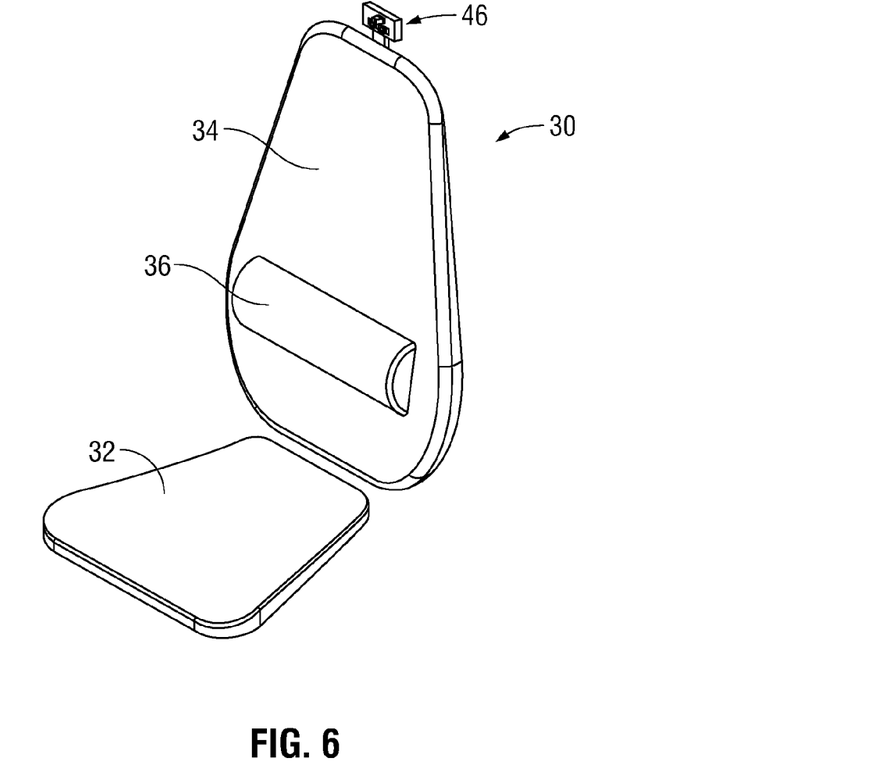
FIG. 6 provides an illustration of another embodiment of the ergonomic seat pad.

An embodiment of the present invention includes an ergonomic chair pad 30 configured such that the ergonomic chair pad can be attached to a chair. The ergonomic chair pad can be formed of any suitable material, such as fabric, foam, leather or plastic. An ergonomic chair pad of the present invention includes at least two portions, hereinafter referred to as either portions or pads. One pad 32 generally corresponds to the seat portion of a chair and another pad 34 generally corresponds to the backrest portion of a chair. Embodiments of the ergonomic chair pad 30 of the present invention can be formed as a single unit, with a seat pad 32 and a back pad 34 connected at a fold in the chair pad material, as separate pads operably connected to one another, or a separate pads adapted to be positioned so as to operate with each other according to the present invention. As shown in FIG. 6, the ergonomic chair pad 30 can also include, in a further embodiment, a separate additional attachable lumbar pad 36 that may be positioned with respect to or attached to either the seat pad 32 or the back pad 34, or both.

The ergonomic chair pad 30 includes one or more electronic sensors. These sensors can be embedded in the chair pad, or attached to the surface of the chair pad. In one embodiment, the seat pad includes two seat pad sensors. The first seat pad sensor 38 is generally located in the front portion of the seat pad corresponding to the front of the seat of a chair and the back of a user's legs. This first seat pad sensor 38 is placed in such a way that it is activated when a user is seated in the ergonomic chair pad. This first sensor 38 can be used for a variety of purposes, for example to determine whether a user is seated in the chair. The first seat pad sensor 38 can be used to activate the other electronic components of the ergonomic seat pad 30 at the time that a user sits in a chair to which the ergonomic seat pad 30 is attached. The first seat pad sensor 38 is preferably a switch, but could also be a pressure sensor or a force sensing resistor.

The seat pad 32 can also include a second sensor 40, generally located in the rear portion of the seat pad 32 corresponding to the rear of the seat of the chair and the lower posterior portion of the user's body. This sensor 40 can be used to determine whether the user is seated in such a way that his posterior is against the back of the seat portion of the chair and touching the backrest portion of the chair, as is generally considered to be ergonomically correct. The second seat pad sensor 40 is preferably a switch, but could also be a pressure sensor or a force sensing resistor. Additional sensors can be located in the seat pad 32 to improve the sensing capability of the seat pad and increase the amount of data that is collected.

In embodiments shown in FIGS. 3A, 3B, 4 and 6, which include a lumbar pad 36, the lumbar pad 36 includes a third sensor 42, which can be used to determine whether the user is seated in such a way that the lumbar region of her back is properly positioned to maintain an ergonomically correct seated posture. The third sensor 42 is preferably a force sensing resistor, but could also be a pressure sensor or a switch. Additional sensors can be located in the lumbar pad 36 to improve the sensing capability of the lumbar pad 36 and increase the amount of data that is collected.

In a further embodiment, the ergonomic chair pad includes a fourth sensor 44, located in the upper portion of the seat back pad, which can be used to determine the distance between the user's upper back or shoulder blades and the surface of the seat back pad 34. This distance is used to determine whether the user is seated in such a way that their shoulder blades or upper back is properly positioned in an ergonomically correct seated posture. Preferably, this fourth sensor 44 is an infrared sensor.

Figure 11:
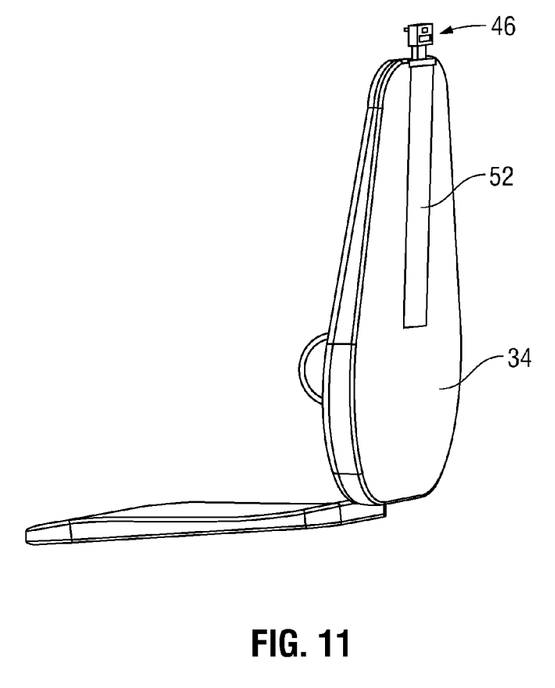
FIG. 11 provides an illustration of the back of the embodiment of the ergonomic seat pad of FIG. 6.
Figure 12:
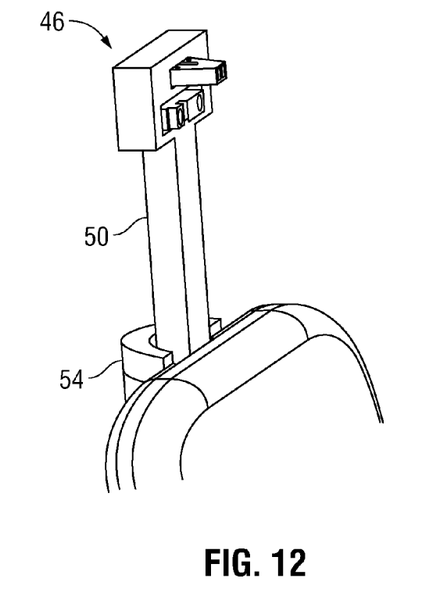
FIG. 12 is a close-up illustration of an embodiment of the adjustable neck-sensor which includes a Velcro strap for fixation of the adjustable neck-sensor in a position suitable for a particular user.

In a further embodiment, the ergonomic chair pad 30 includes a neck-position sensor 46 (See FIGS. 6, 11, and 12). The neck-position sensor 46 may be operably attached to the backrest pad 34 and may be adjustable so that it can be raised and lowered to position the neck-position sensor 46 to be at the same height as the back of the neck of a user that is seated in a chair to which the ergonomic chair pad is attached. The neck-position sensor 46 is preferably attached to an acrylic shaft 50, which is slidably inserted into a fabric sheath 52 incorporated into the back side of the backrest pad 34. The fabric sheath 52 extends to the midline of the backrest pad 34 to maintain its adaptability and usability for various chairs. The backrest pad 34 includes a Velcro strap 54 or other fixation means, for holding the acrylic shaft in a fixed position, thereby fixing the position of the neck sensor 46 at a proper height for any particular user of the ergonomic seat pad 30. The neck position sensor 46 is preferably an infrared sensor, but may be any suitable sensor capable of determining the distance between the sensor and the back of the user's neck or the position of the user's neck when the user is seated in the ergonomic chair pad. The ability to adjust the height of the neck sensor in order to accommodate users of different heights is particularly useful when the ergonomic chair pad is used to train and educate children or young adults about proper posture.

Figure 7:
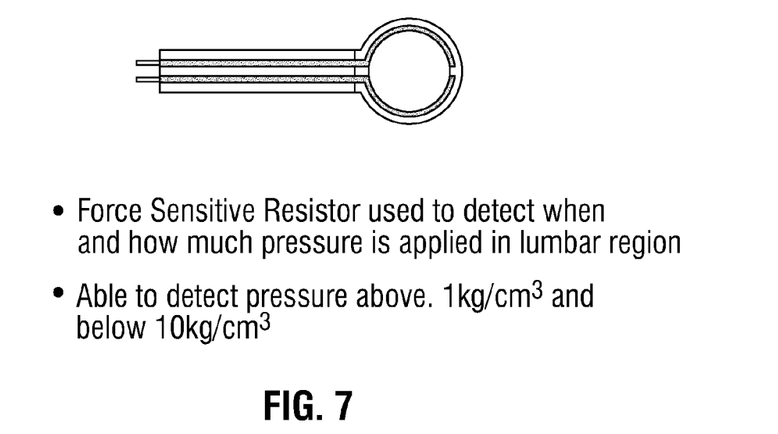
FIG. 7 provides an illustration of a force sensitive resistor.

As will be understood by one of ordinary skill in the art upon reading this disclosure, additional sensors may be included throughout the ergonomic seat pad to provide more data and/or a more detailed and complete indication of whether the user is seated in an ergonomically correct posture. As will also be understood by a person of ordinary skill in the art reading this disclosure, the above-described sensors may be pressure sensitive sensors, normally-closed sensors, force resistive sensors as shown in FIG. 7, or other sensors known in the art for accomplishing the needs of the various embodiments of the present invention.

All of the above-described sensors may be operably connected to a microprocessor. The microprocessor can be located either within the ergonomic chair pad, or can be separately attached to it. The microprocessor may be configured to receive and measure signals from the sensors to which it is connected and thereby assess the amount of pressure that a particular user is applying to each sensor. This pressure corresponds to the location of a user's limbs and back and can be used to evaluate whether a user is sitting in the chair with an ergonomically correct posture. The microprocessor may include on-board memory. The microprocessor may be configured to be operably connectable to a personal computer. As one of ordinary skill in the art will appreciate, this operable connection can be accomplished either by a wire connection, such as a USB cable, or by a wireless connection, such as an IEEE 802.11 WiFi connection, a Bluetooth connection, or by other suitable means. In one embodiment, the microprocessor is an Arduino USB Duemilanove board.

Figure 5:
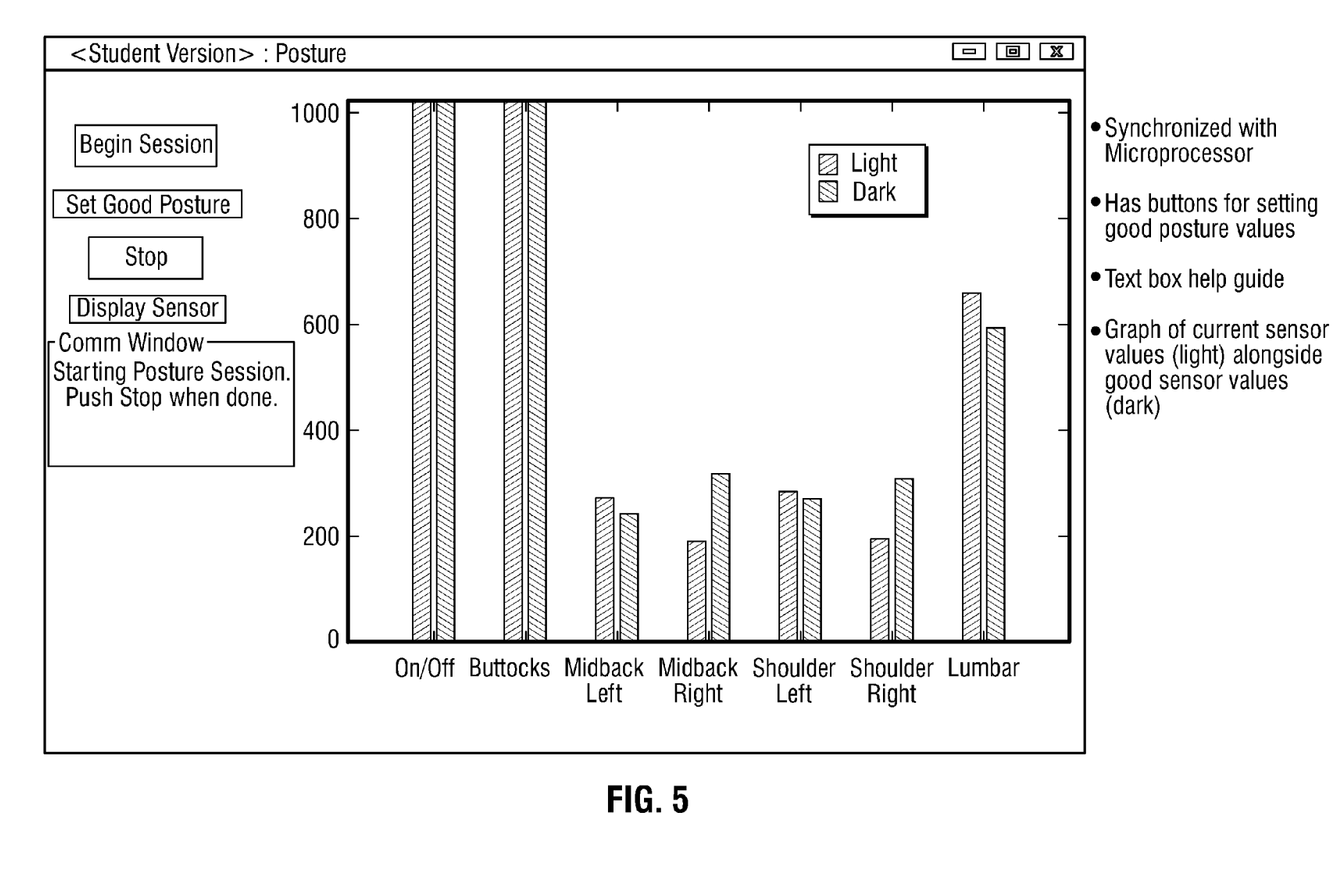
FIG. 5 provides an illustration of one screen of the graphical user interface.
Figure 5A:
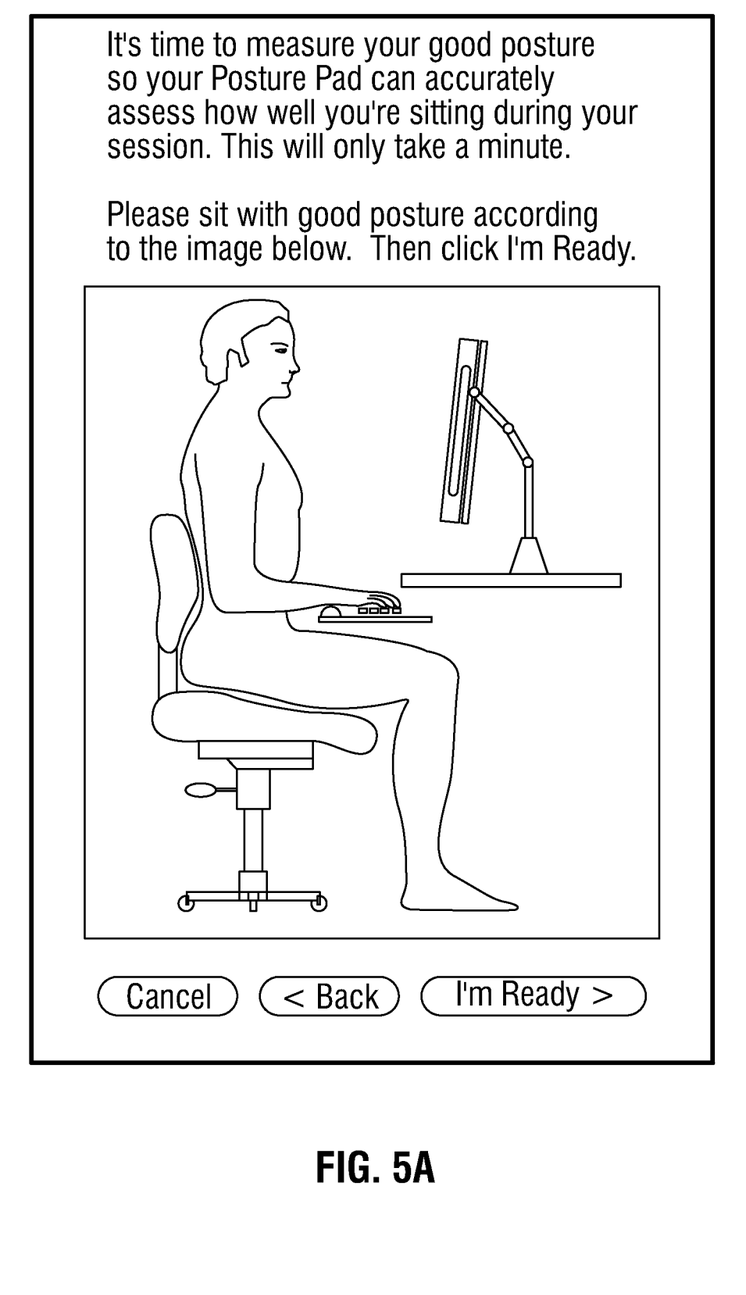
FIG. 5A provides an illustration of a second exemplary screen of the graphical user interface.
Figure 5B:
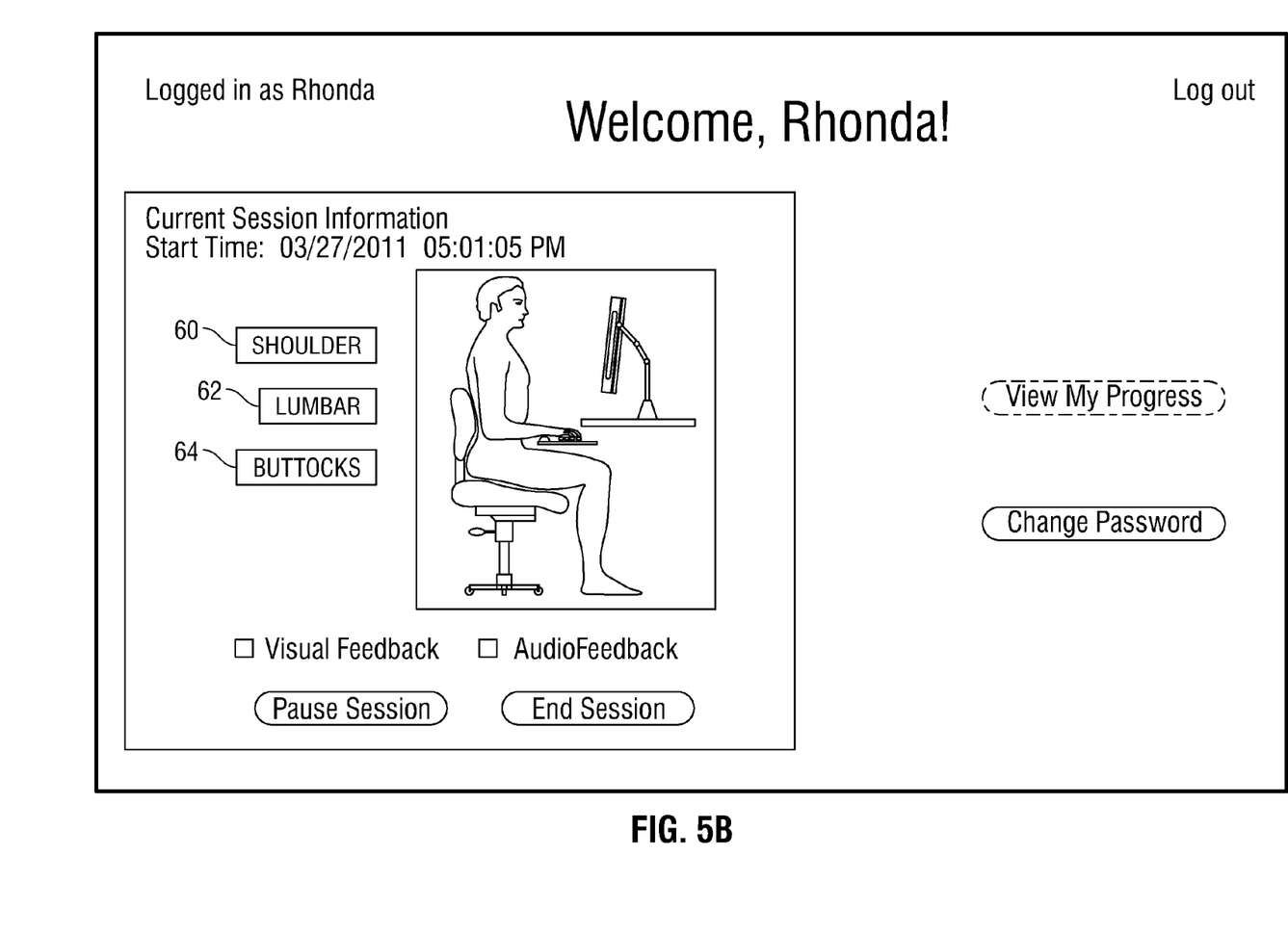
FIG. 5B provides an illustration of a third exemplary screen of the graphical user interface.

The personal computer to which the microprocessor may be connected can be any commonly available personal computer, such as a desktop or laptop computer. In an embodiment, the personal computer is programmed with software to recognize the connection to the microprocessor and to provide a graphical user interface as shown in FIGS. 5, 5A and 5B, which can be manipulated by the computer user that is seated in the chair equipped with the ergonomic chair pad. As shown in FIG. 5, the graphical user interface may be configured to show the user which sensors in the ergonomic chair pad are activated, and the amount of pressure that is present on each sensor. As the user shifts his posture, the information from each of the sensors is received by the microprocessor and the personal computer, then translated into a real-time illustration of the user's posture, via the graphical user interface. As shown in FIG. 5, this illustration can be in the form of a series of bar charts comparing current force against a "good posture" force profile. As shown in FIG. 5B, the graphical user interface can also illustrate whether a user's posture is correct by providing the user with indications that the user's shoulders, lumbar and buttocks positions are correct, by illuminating boxes for shoulder 60, lumbar 62 and buttocks 64 with different color codes, such as using green for proper positioning and red for improper positioning. The personal computer can also be programmed to record sensor information and the information displayed by the graphical user interface, so that this information can be used for subsequent playback or analysis. Preferably, this user will utilize the ergonomic seat pad on multiple occasions, and the information recorded during each such session can be separately recorded, saved, and used to analyze whether a user's posture is improving over a period of time, which could range from hours to months.

Figure 8:
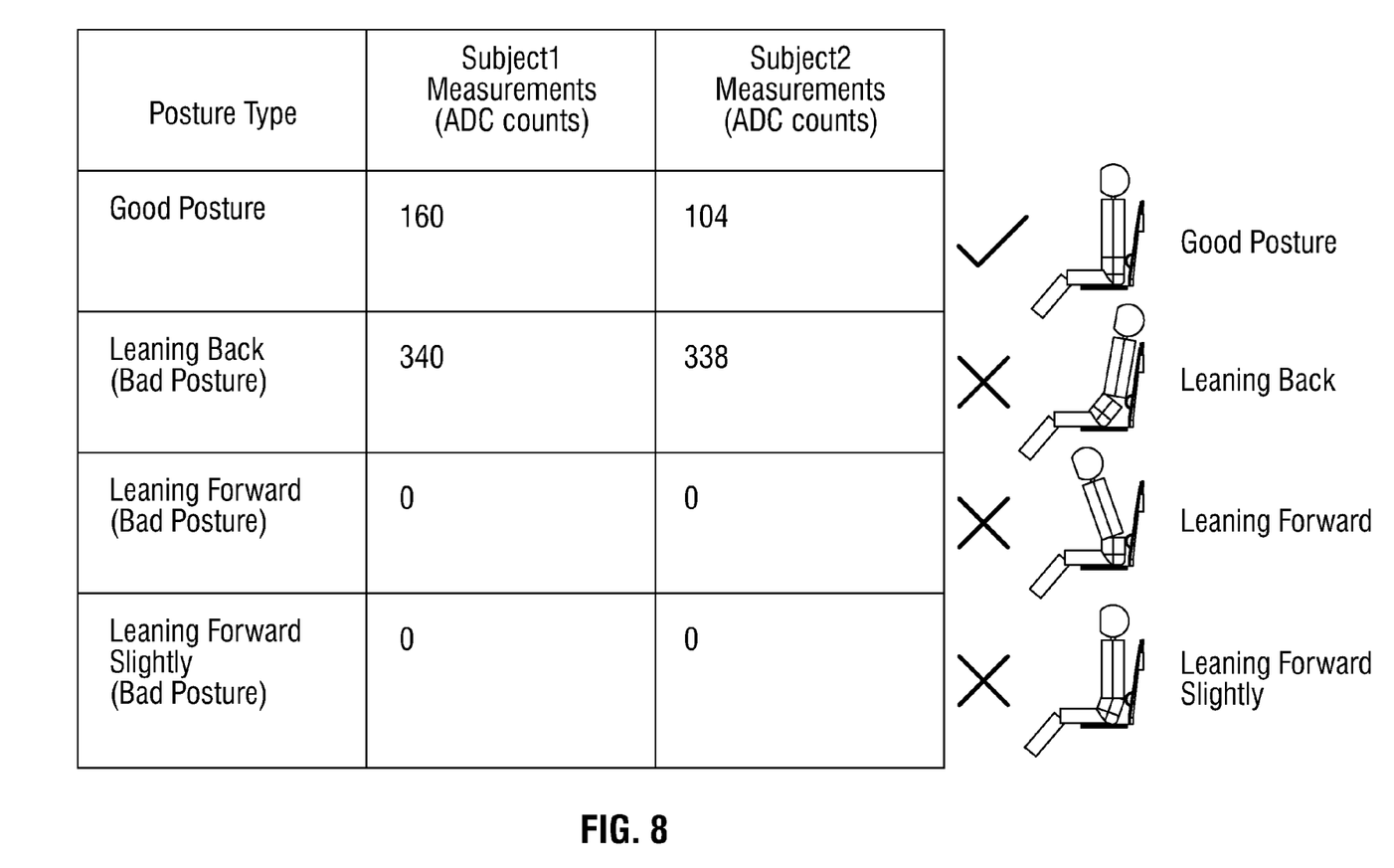
FIG. 8 is a table, showing force measurements taken by an embodiment of the ergonomic seat pad, at the lumbar region, for two subjects and illustrating the different postures indicated by these exemplary force measurements.
Figure 9:
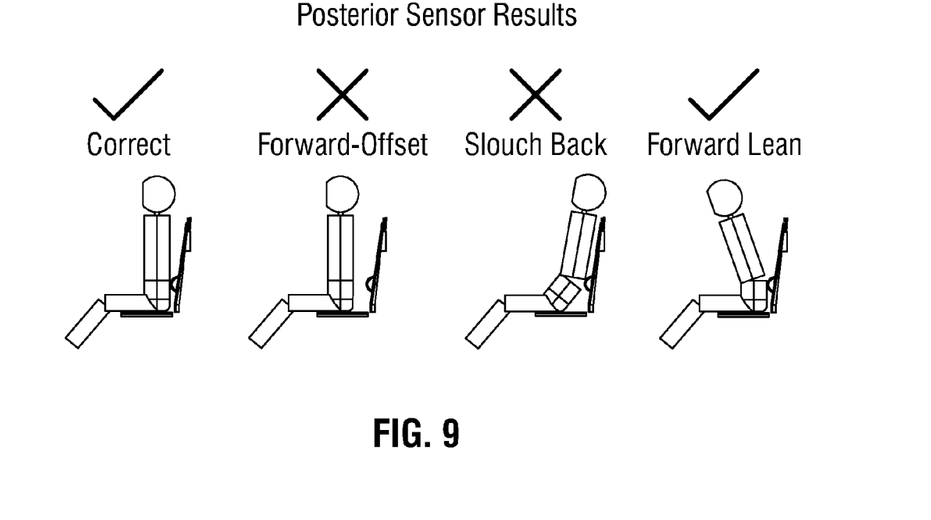
FIG. 9 is a table, showing sensor switch results for the posterior switch of an embodiment of the ergonomic seat pad and illustrating the different postures indicated by these exemplary switch results.
Figure 10:
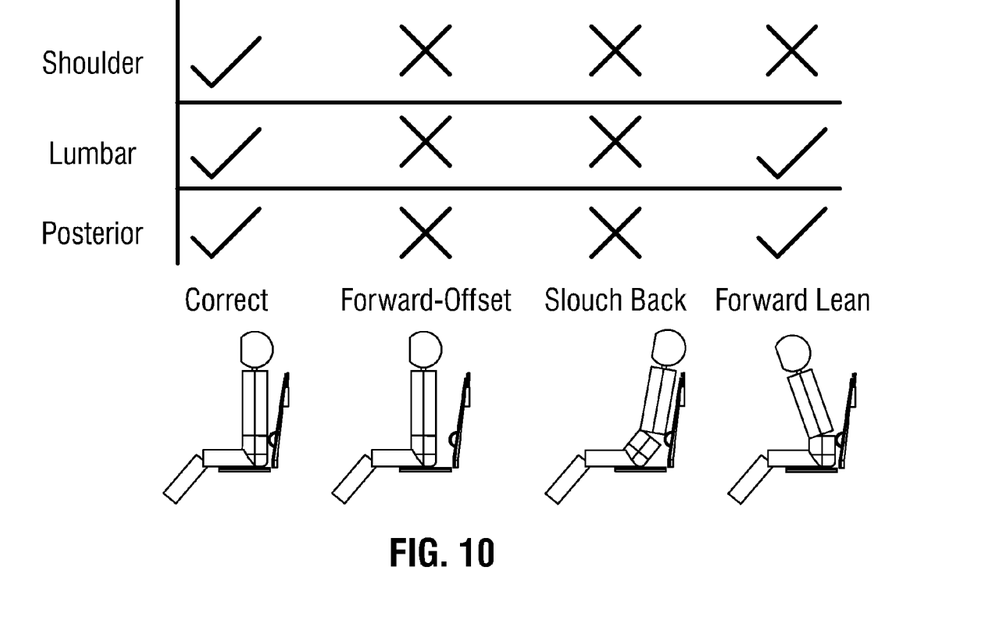
FIG. 10 is a table showing the overall sensor results for an embodiment of the ergonomic seat pad and illustrating the different postures indicated by these exemplary sensor results.

The ergonomic chair pad of the present invention can be used to train and educate a user, including a child or young adult, to adopt and maintain an ergonomically correct posture, based on the seat pad sensor data and recordings, as shown in FIGS. 8-10. This training can be significantly aided by use of a graphical user interface as illustrated in FIGS. 5, 5A and 5B. In an embodiment, this training may be accomplished by carrying out the following steps. First, the ergonomic chair pad and computer are activated. This can be accomplished for example, by an on/off switch, or by using the first sensor in the seat pad to detect the presence of a user seated in the chair with the ergonomic chair pad. Second, the user is instructed to adopt an ergonomically correct posture. This can be done, for example, through messages from the personal computer, signage, or other suitable means. The sensors, the microprocessor of the ergonomic chair pad, and the operably connected personal computer, can be used to sense whether the user has adopted such a posture by comparing the sensor readings of the ergonomic chair pad to stored readings that indicate proper posture. Alternately, the user can adopt a correct posture and then indicate that he has adopted a correct posture through inputs to the personal computer. The personal computer or microprocessor can then record and store the current sensor readings to establish a baseline "correct posture" profile for that user. The correct posture data can also be composed of a compilation or average of data from other users, or baseline data that is entered through the personal computer or which is uploaded or programmed into the software of the system, in advance of the use of the ergonomic chair pad.

In an embodiment, once it has been established that the user has adopted an ergonomically correct posture, the chair pad system displays the sensor readings from the chair pad via a graphical user interface shown on the personal computer screen. See FIGS. 5, 5A, 5B. This graphical user interface can be observed by the seated user to enable the user to maintain his current correct posture. Additionally, the personal computer can be programmed to alert the user when he has slumped, slipped, or otherwise shifted so that he is using less than an ergonomically optimal posture. This alert can be provided on either a real-time basis, or at intermittent intervals, such as when the user has assumed an ergonomically incorrect posture for at least two minutes. This alert can take a variety of forms, including an audible tone issued by either the microprocessor or personal computer, a visual warning on the graphic user interface, a warning light operably connected to the seat pad, or even the actuation of a vibrator embedded in the seat pad.

In a further embodiment, the personal computer is programmed to record and be able to play back all of the sensor readings taken during a period of time while the user is seated. These recordings can be associated with unique user identification information, (see FIG. 5B) which could be, for example, the user's real name, the user's employee number, a unique user name created by the user himself, or an anonymous identification number assigned to the user as part of, for example, a research study. Further, the personal computer can store sensor readings taken during multiple sessions in which the user is seated in a chair equipped with the ergonomic seat pad. This allows the user, a researcher, a teacher, or an employer, to review, at leisure, how the user's posture changes over time. This further allows the user, or other authorized persons, to assess how his posture has improved over a long period of time, to demonstrate that his efforts to adopt an ergonomically correct posture have been successful. Preferably, the user himself is allowed and encouraged to review his own training session posture data on a regular basis to understand how his posture is improving and what adjustments he needs to make in order to maintain proper posture, e.g., for example, to remember not to slump his shoulders forward, or to remember not to lean back too far.

Another exemplary embodiment of the ergonomic chair pad of the present invention provides support in the lumbar, seat pad, and back. Embedded in the pad are sensors connected to a microprocessor. The sensors will be placed in the lumbar, seat pad, and back. The sensors and associated components will include the following:

On/Off sensor 38 in the seat pad 32—A sensor that is in the seat pad, that when sat on will turn the device on, saving battery, or when in neutral position (not pushed) it will be off.

Pressure Sensor 42 in the lumbar—A long strip sensor that senses if the user is leaning back too hard, or leaning too far forward.

Calibration sensors—Sensors that detect the user's size and weight, and adjust the other sensors accordingly.

Ping (or other similar) Sensors 44—A sonar type sensor or infrared sensor that senses how far the neck/back area is from the seat pad.

Bluetooth Technology—Components that connect to the personal computer for calibration and monitoring with visual icons, indicating user's ongoing posture status.

Seating posture tracking capability, with built-in computer/recording device to enable monitoring of users' posture over a period of time in order to enhance the user's training.

Another embodiment of the ergonomic chair pad was constructed as follows. A frame for the embodiment was constructed out of plastic boards to give shape to the seat pad. The seat portion also had a layer of Styrofoam in which to embed electronics. The whole frame was then covered with rubber foam for comfort and with cloth material. The lumbar support was made out of compressed foam, in order to provide firmness. It was covered with a thin layer of cotton batting and then duct tape, and was attached to the seat back with an elastic band, so that the lumbar support can be adjusted vertically to fit the user's body. Switches were embedded into the seat portion and lumbar support so that any improper body positioning would trip the switch and cause a vibrator to activate. Another switch was placed higher on the seat back so that leaning too far back would engage an alarm. In another embodiment, the switches activated three colored lights, rather than an alarm or vibrator. These lights were not visible to the subject. This allowed a researcher observing the user subject to differentiate changes in the user subject's posture without the user subjects's knowledge.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative—and not restrictive—the scope of the invention being indicated by the appended claims rather than by the foregoing description, and all changes which come within the meaning and range of equivalency of the claims are therefore intended to be embraced therein.

We claim:

1. A portable system for sensing and training a user to maintain correct posture while seated in a chair with a seat portion and a back portion comprising:
    a first pad attachable to the seat portion of a chair, said first pad having a front area and a rear area;
    a second pad attachable to the back portion of a chair and having a lower area and an upper area;
    a first sensor located in the first pad capable of sensing that a user is seated in the seat portion of the chair;
    a second sensor located in the first pad capable of sensing whether the lower posterior portion of the user's body is in contact with the rear area of the first pad;
    a third sensor operably attached to the lower area of the second pad capable of sensing whether the user's lumbar region is in contact with the second pad;
    a fourth sensor operably attached to the upper area of the second pad capable of sensing a distance greater than zero between the user's upper back and the upper area of the second pad;
    a neck-position sensor operably attached to the second pad and capable of sensing a distance greater than zero between the neck-position sensor and the user's neck, wherein the height of the neck position sensor is adjustable, thereby enabling the system to be used by users of different heights and further comprises:
        a sheath incorporated into the second pad;
        an acrylic shaft that is slidably inserted into said sheath;
        a fixation means for holding the acrylic shaft in a fixed position; and
        wherein the neck position sensor is mounted upon the top end of the acrylic shaft;
    a microprocessor operably connected to the first sensor, second sensor, third sensor, fourth sensor and neck-position sensor and capable of collecting data from each of the first sensor, second sensor, third sensor, fourth sensor and neck position sensor; and
    wherein the microprocessor is configured to transmit the data to a personal computer.

* * * * *